United States Patent [19]
Hare

[11] Patent Number: 5,316,473
[45] Date of Patent: May 31, 1994

[54] LIGHT CURING APPARATUS AND METHOD

[75] Inventor: Robert V. Hare, Georgetown, Del.

[73] Assignee: Dentsply Research & Development Corp., Milford, Del.

[21] Appl. No.: 873,909

[22] Filed: Apr. 24, 1992

Related U.S. Application Data

[63] Continuation-in-part of Ser. No. 609,036, Nov. 5, 1990, abandoned, which is a continuation of Ser. No. 208,201, Jun. 17, 1988, abandoned.

[51] Int. Cl.$^5$ .......................... A61C 1/00; A61C 3/00; A61C 5/00; A61C 9/00
[52] U.S. Cl. ...................... 433/29; 433/215; 433/229; 433/37
[58] Field of Search .............. 433/25, 29, 30, 37, 433/215, 229; 362/806, 811, 362; 385/104, 111, 120; D26/2, 3, 27

[56] References Cited

U.S. PATENT DOCUMENTS

| | | | |
|---|---|---|---|
| D. 222,646 | 11/1971 | Clark, Jr. | D26/4 |
| D. 248,593 | 7/1978 | Oster | D48/33 |
| 1,122,086 | 12/1914 | Dunlop | 433/29 X |
| 1,868,653 | 7/1932 | Abraham . | |
| 2,135,480 | 11/1938 | Birdseye | 176/124 |
| 2,255,657 | 9/1941 | Freedman . | |
| 2,480,393 | 8/1949 | Bossert et al. | 240/2.1 |
| 2,586,723 | 1/1952 | Sakols | 362/32 X |
| 2,840,070 | 6/1958 | Tofflemire | 128/11 |
| 2,885,537 | 5/1959 | Wood, Jr. | 362/32 X |
| 4,375,607 | 3/1983 | Morton et al. | 315/56 |
| 4,445,858 | 5/1984 | Johnson | 433/229 X |
| 4,449,928 | 5/1984 | Von Weissenfluh | 433/40 |
| 4,553,936 | 11/1985 | Wang | 433/229 X |
| 4,592,344 | 6/1986 | Scheer | 433/29 X |
| 4,631,030 | 12/1986 | von Weissenfluh | 433/229 X |
| 4,666,405 | 5/1987 | Ericson | 433/229 |
| 4,673,353 | 6/1987 | Nevin | 433/90 |
| 4,776,792 | 10/1988 | Wagner et al. | 433/37 X |
| 4,784,464 | 11/1988 | Ouchi | 350/96.26 |
| 4,790,752 | 12/1988 | Cheslak | 433/37 |
| 4,802,851 | 2/1989 | Rhoades | 433/93 |
| 4,807,599 | 2/1989 | Robinson et al. | 128/16 |
| 4,813,875 | 3/1989 | Hare | 433/214 |
| 4,852,549 | 8/1989 | Mori | 128/62 A X |
| 4,867,680 | 9/1989 | Hare et al. | 433/37 |
| 4,867,682 | 9/1989 | Hammesfahr et al. | 433/37 |
| 4,885,664 | 12/1989 | Hermanson | 362/123 |
| 4,950,958 | 8/1990 | Lin | 362/806 X |

FOREIGN PATENT DOCUMENTS

0084407 1/1983 European Pat. Off. .

Primary Examiner—Gene Mancene
Assistant Examiner—Nicholas D. Lucchesi
Attorney, Agent, or Firm—Dale R. Lovercheck; Edward J. Hanson, Jr.

[57] ABSTRACT

A light-curing apparatus for curing polymerizable material in the mouth is provided. In one embodiment the apparatus comprises a wand which is substantially the same size as a quadrant or a full dental arch; in a second embodiment, the apparatus is in the shape of a dental tray and is adapted to fit over the outside of a dental tray; and in a third embodiment the light source comprises a portion (substantially the frame) of a double arch impression tray, and has a slide mechanism by which the mesh of a double arch impression tray can be removed from the light source so the light source can be reused. The invention also comprises a method for curing a dental material in the mouth using the apparatus of the invention.

48 Claims, 3 Drawing Sheets

Fig. 11

LIGHT CURING APPARATUS AND METHOD

BACKGROUND

This is a continuation-in-part of U.S. patent application Ser. No. 07/609,036 filed Nov. 5, 1990, now abandoned, which is a continuation of U.S. patent application Ser. No. 07/208,201 filed Jun. 17, 1988, now abandonded.

The present invention relates to light curing of dental impression material, in particular the invention provides a light apparatus adapted for fitting over an impression tray and a method for curing a light polymerizable impression material while the impression material is in contact with an area of which an impression is desired. Beneficially, the invention provides simultaneous substantially even distribution of light over light curable dental impression material while such material is in contact with teeth.

Wang in U.S. Pat. No. 4,553,936, Johnson in U.S. Pat. No. 4,445,858 an Hammesfahr et al in U.S. Pat. No. 4,867,682 disclose apparatus which provide light from only one location at a particular time. Thus, these apparatus are not adopted to provide simultaneous substantially even distribution of light over a U-shaped arch of light curable dental impression material while such material is in contact with teeth as is provided by the present invention.

The use of visible light cured polymeric impression materials such as those disclosed in U.S. Pat. No. 4,813,875 and U.S. patent application Ser. No. 120,269 filed Nov. 13, 1987, both incorporated herein by reference, are gaining acceptance as a desirable means of obtaining a dental impression. Such polymeric materials can be adapted to be dispensed from a syringe or used with an impression tray. Such a visible light cured polymeric impression material is sold under the trademark GENESIS TM by Dentsply International Inc.

It is desirable in many uses to provide the impression material in a disposable tray, and to provide a light source in a more permanently reusable form. Whether the impression material is preloaded in the impression tray in the factory according to U.S. patent application Ser. No. 032,903 filed Mar. 31, 1987, and U.S. patent application Ser. No. 120,304 filed Nov. 13, 1987, assigned to Dentsply International Inc., incorporated herein by reference, or loaded by the practitioner immediately before use, a key to the convenience and usability of such a material is a rapid cure to a strong and elastomeric material when actinic light is applied to the material at the convenience of the practitioner. In the past, such actinic light was provided as a point source, such as is the conventional adaptation of a PRISMETICS ® LITE apparatus, available from The L. D. Caulk Company, a division of Dentsply International Inc. The point source in the PRISMETICS ® LITE apparatus is a light-issuing tip having a diameter of less than about 1.5 cm. When a point light source can be used, the practitioner must move the point source from point to point over the impression tray to cure all the material in the tray. Although it may take only 10–20 seconds at a particular point to cure that portion of the impression material sufficiently, in a typical full dental arch tray, which has hard-to-reach areas and a surface area of about 60 cm$^2$, it may take as much as 2–5 minutes, or more, to cure all the impression material in the tray. Also, in some circumstances, it is desirable to cure the impression material evenly over the whole surface rather than cure one side of the tray, and then the other side of the tray in sequence.

In prior art point source devices, used alternately to cure small fillings in the mouth, the intensity of the light source is limited by its possible effect on the retina of the human eye. Sources with intensity greater than about 1 w/cm$^2$ may be hazardous and accordingly fall outside the Commercial National Standard draft specifications and ADA Standards for such devices.

It is an object of the present invention to provide an apparatus and a method to rapidly cure impression material while making a dental impression.

It is a further object of the present invention to provide an apparatus and a method simultaneously and uniformly cure all of the impression material in a dental tray while making a dental impression.

It is another object of the invention to increase substantially, uniformity of emission of light issuing from a high intensity source to be substantially evenly distributed over at least a large portion of a U-shaped dental arch without necessarily increasing the overall (average) intensity of the light per unit area.

SUMMARY OF THE INVENTION

The present invention relates to a visible wavelength light source comprising an element having a generally curved shape and having a size adapted to fit into a mouth. The element has means for transmitting light from substantially every portion of the element onto a material which is to be light polymerized in the mouth. In a preferred embodiment, the light source is in U-shape in the form of a dental arch or a portion of a dental arch. In one embodiment, the element comprises a plane wherein the light transmitted is transmitted from a single plane which is adapted to be parallel to the alveolar ridge.

In a preferred embodiment of the invention, the element comprises a trough, having a bottom and sidewalls, which is adapted to fit over the outside of an impression tray and to transmit light through the bottom and sidewalls of the trough at substantially normal angles into the impression tray.

Light may be transmitted through fiber optics or by including a light-emitting device or devices such as a tungsten/halogen vacuum bulb, light emitting diodes or the like, within the element in the shape of the element. Light may also be transmitted using mirroring of the sides and bottom of the trough. Mirroring may also be used advantageously in combination with other light transmitting or emitting sources such as those given by way of example above.

In a preferred embodiment of the invention the light source comprises a frame for double arch impression tray. In such an embodiment, in its most preferred form, a mesh contains impression material on both sides for taking the impression of the upper and lower arches of teeth or portions of the upper and lower arches. The mesh is desirably carried by a frame when positioned in the mouth and after the impression is taken the mesh is removed from the frame. The frame provides a light source and when the mesh is removed a new mesh may be inserted and the frame reused. In such an embodiment the frame may contain a light bulb contoured in the shape of the frame, or fiber optic bundles may comprise the shape of the frame wherein, for example, fiber optic ends from the bundle may be evenly distributed throughout the surface of the frame. As in the above-described embodiments, the outside surface, the wings in the case of double arch impression tray frame, may be mirrorized to optimize the utilization of the light.

A method of polymerizing a light polymerizable material in an impression tray is provided in accordance with the invention. The method uses a U-shaped light source in conjunction with an impression tray. By placing the light source in close proximity to the impression tray, and transmitting light from the light source to the impression material it is polymerized in the impression tray.

The apparatus and method of the invention make it possible to cure all of the impression material in an impression tray substantially at the same time, and to reduce the amount of time and difficulty required to cure the impression material.

DETAILED DESCRIPTION OF THE INVENTION

Dental arch shaped light distributors in accordance with the invention all adapted to provide substantially uniform light intensity over substantially the entire lower and side surfaces of light curable dental impression material while positioned in a patient's mouth. Substantially uniform distribution of light intensity is accomplished by providing uniform distribution along the length of each side of a dental arch, light emission means which emit substantially equal light intensity such as light sources and/or optical fiber ends from which light is emitted.

In a U-shaped light distributor in accordance with the invention light is emitted uniformly from a plurality of light emission means uniformly positioned along each of the sides. Each of the two sides of the U-shaped light distributor is a mirror image of the other side. Thus, light of substantially equal intensity is emitted from each of a plurality of uniformly distributed points on both sides of the U-shaped distributor and at all such points is emitted immediately adjacent to light curable dental impression material. This simultaneous uniform emission of light simultaneously uniformly cures the entire U-shaped light curable dental impression material positioned adjacent to the U-shaped light distributor.

Figure 1:
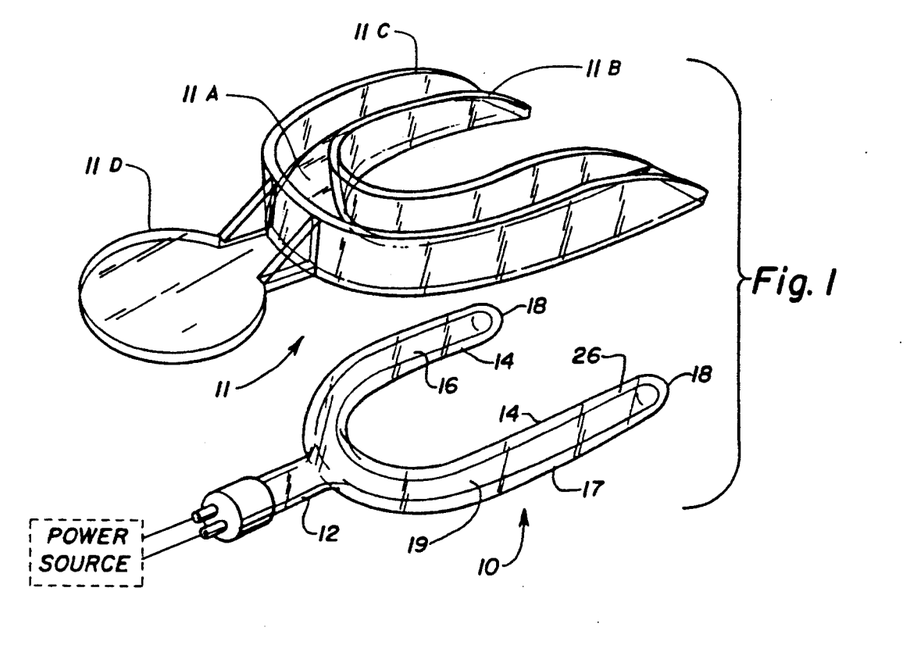
FIG. 1 is a perspective view of an element of the invention containing a light proximal to an impression tray.

Referring to FIG. 1, a light element (wand) 10 and tray 11 are seen. Tray 11 has a U-shaped bottom wall 11A integrally connected to inner and outer U-shaped side walls 11B and 11C respectively. Outer side wall 11C is connected to tab 11D. Light element 10 has a stem 12 and two side arches 14 which are joined to form a U-shaped full dental arch containing a light bulb 16. Stem 12 provides means for the practitioner to hold the apparatus when it is used and means for containing the wires that supply electricity to light bulb 16. It is desirable that light bulb 16 be conformed to the U-shape of said full dental arch and be completely sealed within element 10 when in use, and that top 26, bottom 17, sides 19 and end plate 18 completely encase bulb 16. Light element 10 is shown in close proximity to impression tray 11 in a position similar to that which will be used to cause curing of the impression material in the tray.

Those skilled in the art will recognize that means may be provided to open element 10 to replace bulb 16. For example, top 26 may have a snap fit connection to bottom 17 throughout side 19.

While element 10 is designed primarily to provide actinic light through bulb 16, those skilled in the art will recognize that bottom 17 and sides 19 of element 10 are preferably mirrored to enhance the effect of the light emitted through top 26 from light 16. Of course in another alternate form, the bottom 17 could also be planar for special uses. Bulb 16 may comprise a filament containing bulb and/or a gas containing bulb wherein the gas contained therein is activated to generate light (for example, a fluorescent light).

Figures 2, 3:
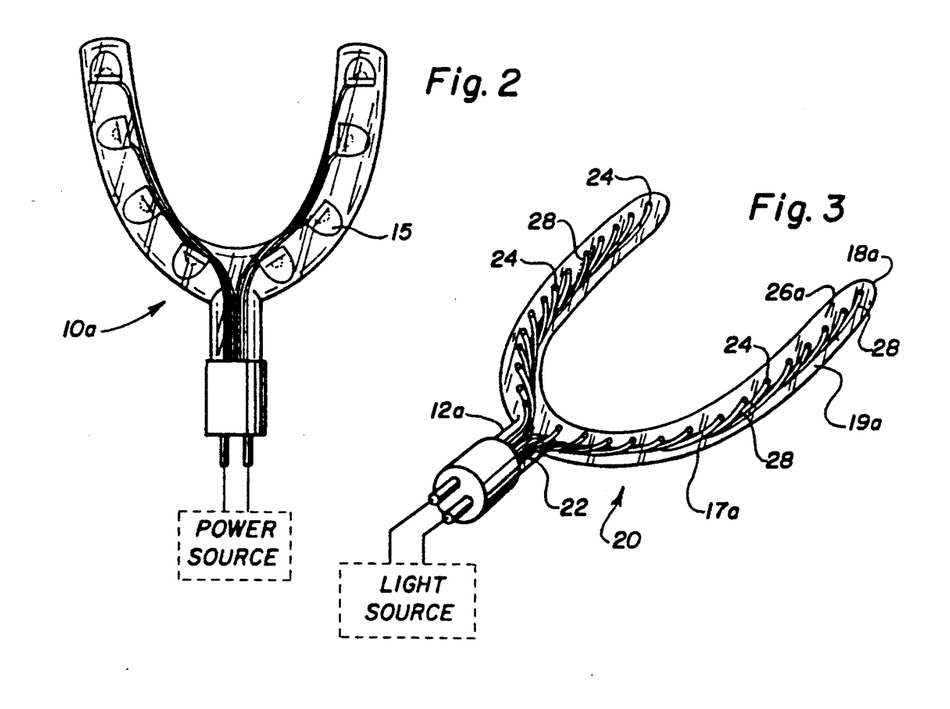
FIG. 2 is a plan view of an alternative light-containing element of the invention.
FIG. 3 is a perspective view of an element of the invention containing optic fibers.

An alternative element embodiment is illustrated in FIG. 2. Element 10a includes a series of light sources 15. Light sources 15 may be a series of light bulbs or a series of light emitting diodes.

In the illustrated embodiment of FIGS. 1 and 2, top 26 of element 10 is a substantially planar surface throughout the dental arch shape of the apparatus. In its use, the apparatus is held next to a dental tray after the dental tray has been positioned to take a dental impression of an upper or lower arch. The light bulb 16, which preferably produces light in the visible wavelength range, preferably a wavelength of 360–600 nm, is then turned on for a time sufficient to cure the dental impression material. Those skilled in the art will recognize that the apparatus may be provided in the shape of a partial dental arch, such as that illustrated in FIG. 8 for a different embodiment.

Referring now to FIG. 3, a fiber optic element 20 of the invention is illustrated comprising a stem 12a and an optic fiber bundle 22 contained within stem 12a. Optic fibers 28 extend from bundle 22 and are distributed substantially evenly in top 26a where optic ends 24 attach to top 26a. It is desirable that ends 24 be connected substantially perpendicular or normal to the tray surface so that maximum penetration of light into the impression material is achieved Element 20 is structured similar to element 10 having bottom 17a, end 18a and sides 19a with top 26a providing a substantially planar surface.

Figure 8:
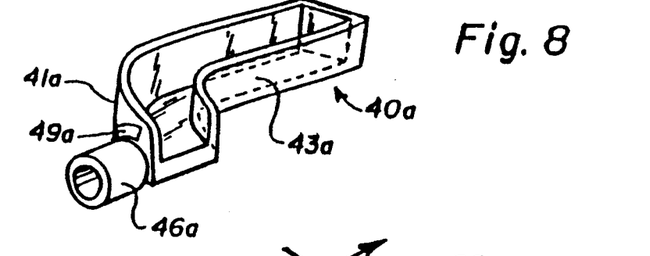
FIG. 8 is a perspective view of an element of the invention in the shape of a partial dental arch.

Element 20 is in one preferred use used substantially in the same manner as element 10, transmitting light substantially from a plane conforming to or comprising the curved U-shape of the dental arch or portion of a dental arch. In both cases, if desired, the practitioner may supplement the light transmitted from the element with another light apparatus (such as Prismetics® light) along the sides of the impression tray after, before or simultaneous with the application of light from element 10 or element 20. Bottom 17a, sides 19a and end 18a may be mirrored to enhance the effects of the transmitted light. The element may also be provided in the shape of a partial dental arch as is illustrated in FIG. 8 for a different embodiment.

Figure 4:
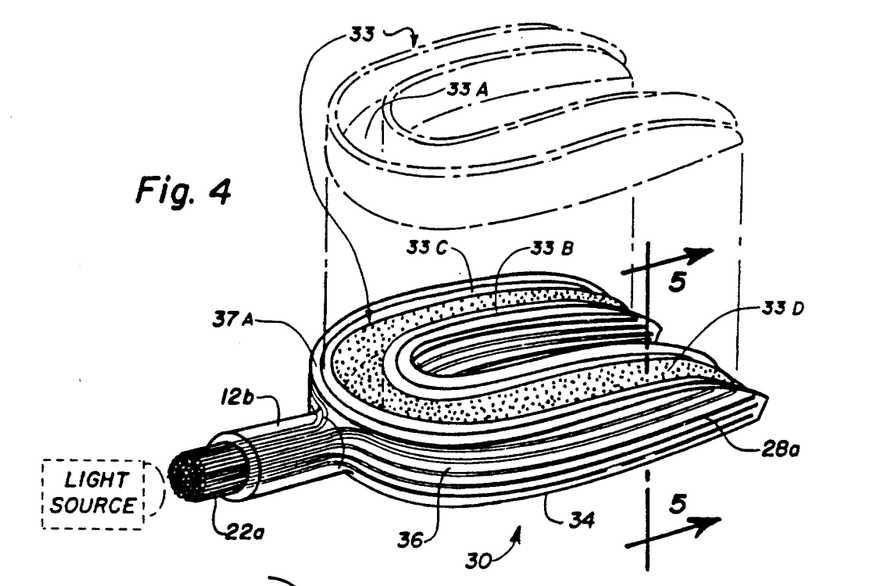
FIG. 4 illustrates a loaded impression tray seated inside an element containing optic fibers.
Figures 5, 6, 7:
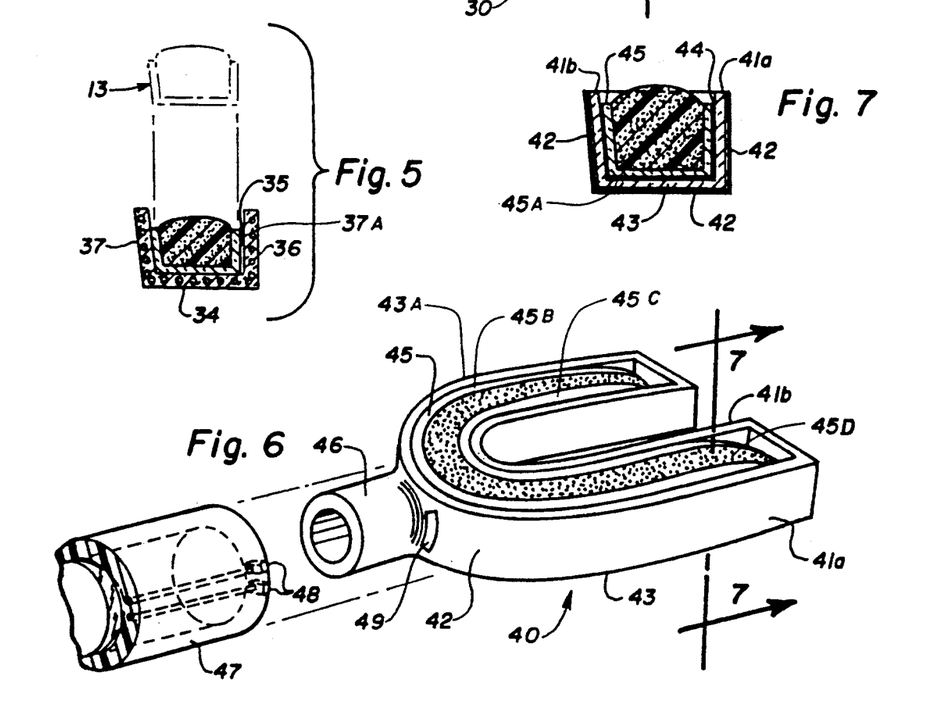
FIG. 5 is a sectional view taken on line 5—5 of FIG. 4.
FIG. 6 illustrates a loaded impression tray seated inside an element which has a mirrored surface.
FIG. 7 is a section taken on line 7—7 of FIG. 6 showing the outside mirrored surface.

Referring now to FIGS. 4 and 5, tray-shaped fiber optic element 30 comprises a stem 12b containing a fiber optic bundle 22a; and, bottom 34, and sides 36 and 37 which together form housing 37A and enclosed trough 35 in the shape of a dental arch. The sides 36 and 37 of element 30 are dimensioned so that they fit over the outside of light transparent dental tray 33 which is illustrated within element 30 and above element 30 in phantom lines. Tray 33 has a U-shaped bottom wall 33A integrally connected to inner and outer U-shaped side walls 33B and 33C respectively. Tray 33 supports photopolymerizable impression material 33D. Tray 37A is adapted to be positioned within trough 35 of housing 37A. Optic fibers 28a from bundle 22a are directed to and are embedded in bottom 34, sides 36 and 37 in a substantially even distribution to provide actinic light over substantially the whole surface area of trough 35. In the illustrated embodiment, optic fibers 28a are an unclad acrylic type, glass type or a similar type of optic fiber, that transmits light through the wall of the fiber. Those skilled in the art will recognize that clad optic fibers, which transmit light substantially end to end of the fiber may be used in the embodiment of FIG. 4. In such a case, the ends of the optic fibers will be attached to the element in a manner similar to that illustrated in FIG. 3. Sides 36 and 37 and bottom 34 preferably have mirrored surfaces to enhance the effect of the light transmitted into trough 35, and the element may be provided in the general shape of a partial dental arch (quadrant) as is illustrated by element 40a in FIG. 8.

In its use, after an impression tray filled with impression material is positioned on the area of which an impression is desired, element 30 is placed over the impression tray with the sides 36 and 37 encompassing the sides of the impression tray and bottom 34 adjacent to the bottom surface of the impression tray. Actinic light is then passed through the impression tray for a time sufficient to polymerize the impression material.

In another embodiment, using high intensity light, an element having only mirrored surfaces, as illustrated by element 40 in FIGS. 6 and 7 may be used.

Referring now to FIGS. 6 and 7, element 40 comprises outside side surface 41a in the shape of a dental arch having mirrored surface 42 and mirrored inside sides 41b also in the shape of a dental arch, sides 41a and 41b being connected to bottom wall 43 forming housing 43A and enclosing trough 44 therebetween. It will be understood that as shown the mirrored surface 42 covers walls 41a, 41b and 43. In the illustrated embodiment, sides 41a, 41b and joining wall 43 are dimensioned to permit seating of impression tray 45 within trough 44. Tray 45 has a U-shaped bottom wall 45A integrally connected to inner and outer U-shaped side walls 45B and 45C respectively. Tray 45 supports photopolymerizable dental impression material 45D. Tray 45 is adapted to be positioned within trough 44 of housing 43A. Stem 46 is adapted to receive a light source 47 having a very high intensity. Because of the high intensity of light source 47, as a safety feature, light source 47 has terminal 48 which completes an electrical circuit when they contact plate 49 on element 40. Accordingly, light source 47 cannot be activated unless connected to element 40.

FIG. 8 is an illustration of a quadrant light element 40a which is constructed in the same manner as full arch element 40 of FIG. 6. Stem 46a, mirrored sides 41a and 43a, and plate 49a have the same function as similar parts illustrated in FIG. 6.

Figure 9:
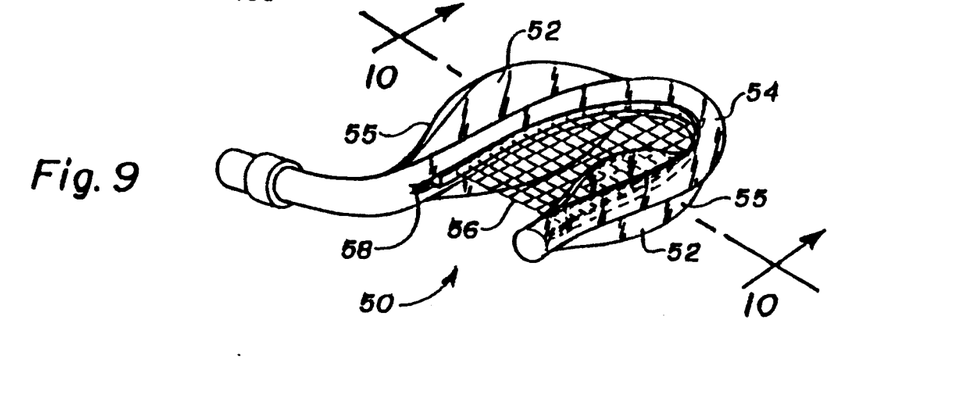
FIG. 9 is a top view of a double arch impression tray containing a light source means.
Figure 10:
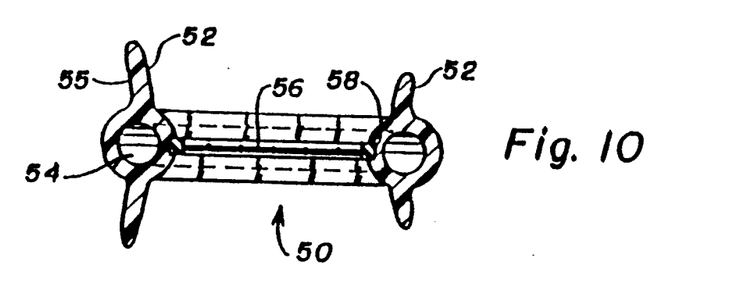
FIG. 10 is a sectional view taken on line 10—10 of FIG. 9.

Referring now to FIGS. 9 and 10, an impression tray known as a double arch impression tray is illustrated. A double arch impression tray is used to obtain an impression of upper teeth and lower teeth while at the same time establishing the bite relationship between the upper and lower teeth (i.e. a triple function). Double arch impression tray light source 50 comprises wing 52 on each side thereof which is made of a flexible material, such as a flexible plastic, which conforms to the shape and size of the patient's mouth; mesh 56 which holds impression material on its upper and lower surfaces; and in the illustrated embodiment, light bulb 54 which is formed in the shape of the double arch impression tray and comprises a substantial part of its frame; and slide 58 which permits separation of mesh 56 from light source 50 so that light source 50 can be reused simply by inserting a new mesh 56 into slide 58 when a new impression is desired. Wings 52 may desirably have a mirrored outside surface 55 which increases the efficiency of the light source.

When used, the tray is put in position for taking an impression, and light in the visible spectrum is preferably applied using parameters described below for a period of time calculated as described below.

The tray may be sterilized, as is the case with each of the embodiments described herein, by well-known techniques of cold sterilization or by other means known to those skilled in the art.

Figure 11:
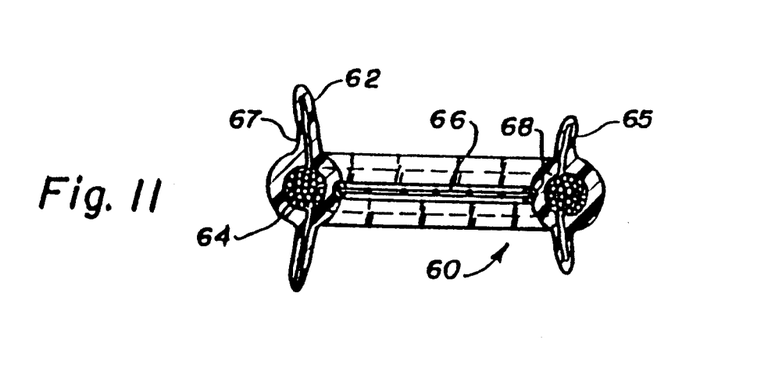
FIG. 11 is a top view of a double arch impression tray containing light-transmitting optical fibers.

In an alternative embodiment of a double arch impression tray light source 60 as illustrated in FIG. 11, instead of using a light bulb, light may be transmitted into the tray by optic fibers 67 which are attached to the tray through fiber optic bundle 64 which provides a frame for double arch impression tray 60. Optic fibers 67 are attached to wings 62 in a substantially even distribution, and in the preferred embodiment, wings 62 will have outside mirrored surfaces 65 which reflect actinic light into impression material contained on mesh 66. Slide 68 permits the separation of mesh 66 from light source 60 when an impression is completed, and permits the reuse of light source 60 for taking additional impressions.

Those skilled in the art will recognize that optic fibers may be provided which substantially contain light within the fiber to be delivered from the end thereof (e.g. clad optic fibers), or may be provided in a form where light is delivered through the walls of the fiber (e.g. unclad optic fibers). As described herein, clad glass type optic fibers are preferred for use in light sources 20, and unclad acrylic type light fibers are preferred in light sources 30, 50 and 60.

In the embodiments where light is piped into a tray from an outside point source, such as the mirrored light source such as light source 40, or the fiber optic light sources such as light sources 20, 30, 50 and 60, means may be provided, similar to that illustrated for element 40 to prevent activation of a point source light (which can be connected to the fiber optic bundle, for example) unless a connection is made between the point light source and the fiber optic bundle. This may be provided as a safety feature so that the operator and the patient will not be exposed to potentially harmful high light intensity from the point source.

Materials used to make the light sources described herein may comprise materials known in the art for making dental impression trays. Also, although illustrated as being made of a substantially rigid material, those skilled in the art will recognize that many of the embodiments described herein (especially elements containing optic fibers) may be made of a substantially flexible material that permits the light element or source to conform substantially to the shape of an impression tray, or may comprise a fiber optic mat with a minimal, or no plastic coating.

Using the apparatus of the invention, it is theoretically possible to cure dental impressions and the like to a clinically acceptable state in less than 60 seconds, preferably less than 30 seconds, and more preferably less than 10 seconds and even more preferably 5 seconds or less and most preferably less than 1 second.

For safety it is preferred that the light intensity transmitted or emitted from the surface of a light source element be no more than about 1 watt per square centimeter (w/cm$^2$), and preferably the intensity will be about 0.5 w/cm$^2$ and most preferably about 0.25 w/cm$^2$. Also to provide superior safety the light should be substantially limited to the visible light spectrum of 360-600 nm. The present invention has especial utility with a light transmitting area about 5 to 80 cm$^2$, preferably about 5 to 60 cm$^2$.

EXAMPLE

A light curing elastomeric impression material described in copending U.S. patent application Ser. No. 120,269 filed Nov. 13, 1987, is marketed together with suitable impression trays and other accessories under the trademark "GENESIS TM" by The L.D. Caulk Company Division of Dentsply International Inc. The impression material is placed into a clear impression tray and cured by moving a point source over the surface of the tray to obtain a satisfactorily cured dental impression. The point source recommended is a PRISMETICS® lamp with an output of about 500 milliwatts per square centimeter (mw/cm$^2$) in the visible spectrum, between 360 and 600 nm wavelength. The PRISMETICS® light has an issuing tip having an area of about 0.8 cm$^2$. When a quadrant tray, such as would mate with the quadrant light of FIG. 8, is used to contain the impression material, it presents a tray surface area in contact with a like outwardly exposed surface area of dental impression material of surface of about 30 cm$^2$. The material is considered properly cured after about 100 seconds of irradiation. The effective curing power required is then about 500 mw/cm$^2$×0.8 cm$^2$×100 sec=40000 mw sec. (where mw represents milliwatts)=40 w sec. for the entire quadrant tray, or 1.33 w sec/cm$^2$.

THEORETICAL APPLICATION

Using the curing index for the GENESIS TM impression material (1.33 w-sec/cm$^2$), theoretically one can establish the total power (mw sec.) needed for curing trays of the same general construction containing the same polymer having larger surface areas, such as a full tray. From this can be calculated the time needed for curing dental impressions using any light sources of known transmissional area and having a known power rating using the formula $$\frac{A' \times A \times 1.33 \text{ w sec/cm}^2}{P} = \text{number of seconds for cure}$$

wherein A is the surface area of the light element in cm$^2$ and P is the intensity of the light source in watts when a 1 cm$^2$ point light source is used. A' is a ratio, adjusting for the size of the point light source, obtained by dividing the actual area of the point source in cm$^2$ by 1 cm$^2$.

Of course, for each dental impression material and tray the initial calculation will be different and those skilled in the art will recognize that the "curing index" for other curable materials can be established in the same way as described above, and that the above formula can be modified to take into account the efficiency and the light transmitting ability of a particular light source or the efficiency of a particular tray material and impression material to permit light to pass therethrough.

Thus light-curing power of from 5-200 w-seconds, in the specific example provided, more preferably from 20-80 w-seconds is required to polymerize adequately the material in a quadrant tray by moving a point source over the exterior surface.

If one were to increase the intensity of the point source light to 5 w/cm$^2$ a lesser time, for example, only about 10 seconds of irradiation, would be required to cure all the material in the tray. Theoretically, in order to reduce the amount of time required to achieve the same extent of cure to 1 second, the output of the point source light would be about 50 w/cm$^2$. This light requirement is a function of the specific impression composition, the monomers and/or prepolymers used, and their initiators and coinitiators and the size of the specific tray.

In a tray where a point source is attached to the light wand, and the light wand distributes the light delivered, a point source, in a 30 cm$^2$ quadrant light wands having an intensity of about 4 w/cm$^2$ will be needed to effect a cure in about 10-12 seconds.

As described in the present invention, the whole exposed surface of the dental material can be irradiated simultaneously and substantially uniformly to provide a cured object, without the necessity of moving a point source light over the surface. Rather, an impression is placed and then illuminated by means of a light curing wand of the invention. Although the intensity of light applied to each square centimeter of the impression material may be about the same as that of the light conventionally applied by a point light source, this intensity is achieved over the entire surface at substantially the same instant. For example, if an impression tray with a surface area of 30 cm$^2$ is cured adequately with a point source 0.8 cm$^2$ and an intensity of about 0.5 w/cm$^2$ in 100 seconds, a wand or light device of the invention having an area of 30 cm$^2$ delivering an output intensity of 0.5 w/cm$^2$ theoretically would cure the material in about 2.7 seconds. A similar light wand delivering 0.1 w/cm$^2$ would cure the impression in 13 seconds; or if 1.0 w/cm$^2$ were delivered, the impression could be cured in 1.3 seconds.

Impression trays having an impression material engaging surface area of from about 5 cm$^2$ to about 80 cm$^2$ are common in the art. To cure the impression material in such trays in a range of 0.1 to 80 seconds, the present invention may theoretically utilize point light sources having intensities of about 0.5–140 w/cm², preferably about 1–90 w/cm², and most preferably about 2–70 w/cm².

In the case where higher powered lamps are used to illuminate the surface uniformly, the impression material can be cured in shorter time. Shortened residence times are more comfortable to the patient and can reduce labor costs and chair time for the dentist. In the case that times can be reduced to about 1–60 seconds, more preferably 1–30 seconds, and even more preferably 1–10 seconds there is substantially no need to physically maintain the tray in place over a long period of time as is the case with longer cure times to preserve the relationship between the impression material and the dental structure of which an impression is being taken.

While being described primarily as an apparatus and method for taking a dental impression, those skilled in the art will recognize that the same procedures can be used for curing dental materials used to reline dentures or materials associated with orthodontic appliances and other dental materials known to those skilled in the art.

Those skilled in the art will recognize that the intensity of the light source can be adjusted to deliver the intensity of light desired to the impression material depending on the efficiency of the light transmitting means, the size of the element and the curing efficiency of the material.

While the invention has been illustrated and described, it will be recognized by those skilled in the art that this invention may be otherwise variously embodied and practiced without departing from the scope of the following claims.

What is claimed is:

1. A visible wavelength light source for polymerizing light curable dental material within the mouth, comprising:
   (a) an element adapted to support light curable dental material in the mouth and
   (b) means for generating light in said element,
   said element having a U-shape length and a size conforming substantially to the configuration of a dental arch, said element having a U-shaped bottom wall, integrally connected to inner and outer U-shaped side walls, said element having a light emitting surface area of at least about 5 cm², and said means for generating light being integrally connected to said element said means for generating having a light source selected from the group consisting of an optical fiber and a bulb having a filament, said light source being supported by and substantially evenly distributed along said length of said element, and being adapted to transmit light substantially uniformly onto said dental material.

2. The visible light source of claim 1 in which the light source is adapted to transmit light through an impression tray to cure a polymerizable material contained therein.

3. The light source of claim 1 which comprises a planar surface adapted to be oriented toward a dental arch in the mouth and wherein light transmitted from said element is emitted substantially from said planar surface.

4. The light source of claim 3 in which said means for transmitting light comprises optic fibers.

5. The light source of claim 1 in which said element comprises a bottom and sidewalls attached to said bottom on both sides thereof to form a trough, said element being adapted to fit over the outside of a light-transmitting impression tray, wherein said element is adapted to transmit light through a bottom and sidewalls of said impression tray, at substantially normal angles to said bottom and sidewalls of said impression tray.

6. The light source of claim 5 in which said means for transmitting light comprises optic fibers.

7. The light source of claim 5 in which said means for transmitting light comprises mirrored surfaces in said trough.

8. The light source of claim 1 in which said means for generating light comprises means chosen from the group consisting of a vacuum bulb, a number of light emitting devices distributed substantially evenly with regard to a light transmitting area of said light source, or a combination thereof.

9. The light source of claim 1 in which said means for generating light produces a generated light having an intensity of less than about 1 w/cm², said generated light being limited substantially to the wavelengths of about 360–600 nm and comprises a light transmitting area of at least about 10 cm².

10. A method of polymerizing a light polymerizable dental material in the shape of a dental arch while said dental material is in contact with structure in the mouth and providing an outwardly exposed surface, comprising: the steps of sequentially
    (a) providing a light source means for generating light having a U-shape of a dental arch, said shape comprising a plane and light transmitted from said light source being emitted substantially from said plane, said light source comprising a vacuum bulb having the general shape of said plane,
    (b) placing said dental material in a desired position in a mouth,
    (c) placing said light source next to said dental material, and
    (d) transmitting light from said light source substantially, uniformly over at least a substantial portion of an outwardly exposed surface of said dental material to polymerize said material.

11. The method of claim 10 wherein the dental material is dental impression material, reline material or orthodontic appliance material.

12. The method of claim 10 in which said element has a bottom and sidewalls attached to said bottom on both sides thereof to form a trough adapted to fit over the outside of an impression tray, and said light source is adapted to transmit light through said bottom and said sidewalls, at substantially normal angles to said bottom and said sidewalls into said trough.

13. The method of claim 12 in which said means for transmitting light comprises optic fibers.

14. The method of claim 12 in which said means for transmitting light comprises mirrored surfaces in said trough.

15. The method of claim 10 in which said means for transmitting light comprises optic fibers.

16. The method of claim 10 wherein the dental material is polymerized in about 1 minute or less and said light source is operated at an intensity of less than about 1 w/cm².

17. The method of claim 10 wherein said light source comprises a series of light emitting devices distributed substantially uniformly over its surface.

18. A method of polymerizing a light polymerizable dental material in the shape of a dental arch while said dental material is in contact with structure in the mouth and providing an outwardly exposed surface, comprising: the steps of sequentially (a) providing a light source means for generating light having a U-shape dental arch shape,
(b) placing said dental material in a desired position in a mouth,
(c) placing said light source next to said dental material, and
(d) transmitting light from said light source substantially, uniformly over at least a substantial portion of an outward surface of said dental material to polymerize said material said dental material being polymerized in less than about 5 seconds and said light source being operated at an intensity of less than about 0.5 w/cm², having a light transmitting area of at least about 10 cm² and emitting light limited substantially to the wave bands of about 360-600 nm.

19. A visible wavelength light source for polymerizing light curable dental material in the mouth, comprising:
   (a) an element having a shape and size conforming substantially to a U-shaped configuration of a dental arch,
   (b) means for generating light, said means for generating light having at least one filament within a gas containing bulb, said bulb being supported by and positioned within said element, said means for generating light having means to be connected to supply electricity to said bulb, and
   (c) a light transmitting means having a U-shaped bottom member and two side members connected to said bottom member and adapted to be removably connected to said element, said light transmitting means being adapted to hold said dental material in proximity to said element.

20. The light source of claim 19 wherein said light transmitting means comprises an optical fiber web to which dental material may be applied on both sides thereof, and wherein said optical fibers of said web area adapted to emit light from the surfaces thereof to cure said dental material in contact with said optical fiber web.

21. A method of polymerizing a light polymerizable U-shaped dental material while said dental material is in contact with structure in the mouth, comprising: the steps of sequentially
   (a) providing a light source adapted to correspond in general to a U-shape,
   (b) placing said dental material in a desired position in a mouth,
   (c) placing said light source next to said dental material, and
   (d) transmitting light from said light source substantially uniformly over at least a substantial portion of an outwardly exposed surface of said dental material to polymerize said material,
wherein said light is transmitted from said light source in said U-shape and wherein said light source comprises a vacuum bulb having a U-shape.

22. A method of polymerizing a light polymerizable dental material in the shape of a dental arch while said dental material is in contact with structure in the mouth, comprising: the steps of sequentially
   (a) providing a light source means for generating light and having a U-shape,
   (b) placing said dental material in a desired position in a mouth,
   (c) placing said light source next to said dental material, and
   (d) transmitting light from said light source substantially uniformly over at least a substantial portion of an outwardly exposed surface of said dental material,
wherein said light is transmitted from said light source and wherein said light source is selected from the group consisting of a series of light emitting devices and light transmitting optic fibers distributed so as to transmit light substantially uniformly from a surface of said light source.

23. A visible wavelength light source for polymerizing light curable dental material in the mouth, comprising:
   (a) an element having a shape and size conforming substantially to a U-shaped configuration of a dental arch,
   (b) optic fiber means adapted for emitting or transmitting light, said optic fiber means having the shape of a dental arch and being contained within said element, and
   (c) a removable light transmitting means having a bottom member and two side members connected to said bottom member and adapted to be removably connected to said element, said light transmitting means having a shape and size conforming substantially to a U-shaped configuration of a dental arch said light transmitting means being adapted to hold said dental material in proximity to said element.

24. A method of polymerizing method for a light polymerizable dental material while said dental material is in contact with structure in the mouth, comprising the steps of:
   (a) providing a light source means for generating light having a U-shape and sized to fit in a mouth in alignment with at least a portion of a dental arch, said light source being adapted to transmit light and said light source comprises a vacuum bulb having a dental arch U-shape and
   (b) providing means for transmitting light from said light source substantially uniformly over at least a substantial portion of an outwardly exposed surface of said dental material to polymerize said material and
   (c) polymerizing said material.

25. A dental light for polymerizing a light polymerizable dental material while said dental material is in contact with structure in the mouth, comprising:
   (a) a light source having a dental arch U-shape and sized to fit in a mouth in alignment with at least a portion of a dental arch, said light source transmitting light in said arch shape and said light source being selected from the group consisting of a series of light emitting devices and light transmitting optic fibers distributed so as to transmit light substantially uniformly from a surface of said light source and
   (b) means for transmitting light from said light source substantially uniformly over an outwardly exposed surface of said dental material to polymerize said material
   (c) a tray for supporting said material, said tray having a U-shaped bottom wall integrally connected to inner and outer U-shaped side walls.

26. A method for polymerizing light curable dental material in the mouth, comprising the steps of: providing a light source transmitting visible wave-length light and having a shape and size conforming substantially to a configuration of a U-shaped dental arch and sized to fit in the mouth, said light source comprising an unclad optic fiber having a fiber wall which transmits light along its length and delivers light from said fiber wall along its length for polymerizing said light curable dental material in the mouth and polymerizing said material in the mouth.

27. The method of claim 26 wherein said unclad optic fiber is exposed for direct contact with the polymerizing light curable dental material in the mouth.

28. A method of polymerizing a light polymerizable dental material in the U-shape of a dental arch while said dental material is in contact with structure in the mouth, comprising: the steps of sequentially
   (a) providing a light source comprising a vacuum bulb and having a general U-shape in a plane and emitting light substantially from said plane,
   (b) placing said dental material in a desired position in the mouth,
   (c) placing said light source next to said dental material, and
   (d) transmitting light from said light source substantially, uniformly over at least a substantial portion of an outwardly exposed surface of said dental material to polymerize said material.

29. A method of polymerizing a light polymerizable dental material in the U-shape of a dental arch while said dental material is in contact with structure in the mouth comprising the steps of sequentially
   (a) providing an element and a housing having a light source, said element comprising a U-shaped tray
   said housing having U-shaped bottom and inner and outer side walls connected to form a trough adapted to support light curable material, said tray being adapted to be positioned within said trough, said light source comprising a series of light emitting devices adapted to distribute light substantially uniformly over an adjacent surface of said light curable material,
   (b) placing said light source next to said dental material, and
   (d) transmitting light from said light source substantially, uniformly over at least a substantial portion of an outwardly exposed surface of said dental material to polymerize said material.

30. A visible wavelength light source for polymerizing light curable dental material in the mouth, comprising: an element having a bottom member and side members and a shape and size conforming substantially to a U-shaped configuration of a dental arch,
   (a) means for generating light in said element having optical fibers position in a U-shape and adapted to distribute light along at least the majority of said dental arch, and
   (b) a light transmitting means having a bottom member and two side members connected to said bottom member, adapted to be removably connected to said element, said light transmitting means being adapted to be supported by said bottom and side members of said element, and to hold said dental material in proximity to said element.

31. A method of polymerizing a light polymerizable elastomeric dental impression material in the U-shape of a dental arch while said dental material is in contact with structure in the mouth, comprising: the steps of sequentially
   (a) providing an element and a housing,
   said element comprising a U-shaped tray and a housing
   said housing having U-shaped bottom and inner and outer side walls connected to form a trough adapted to support light curable material, said tray being adapted to be positioned within said trough, said housing having a web formed from a plurality of optic fibers having unclad portions and corresponding in general configuration to at least a substantial portion of a dental arch shape,
   (b) placing a dental impression material directly over the unclad optic fiber portions of said web,
   (c) placing said web with said dental impression material thereon in a mouth and forming a dental impression,
   (d) transmitting light from said unclad portions of said optic fiber web and polymerizing the light polymerizable dental impression material and forming an elastomeric dental impression.

32. A dental light for polymerizing light curable dental material in the mouth, comprising: a light source transmitting visible wavelength light and having a shape and size conforming substantially to a dental arch and sized to fit in the mouth, said light source comprising a plurality of at least partially unclad optic fibers formed into a web, each of said unclad optic fibers having a fiber wall adapted to transmit light along at least a portion of its length and to deliver said light from a sufficient portion of the length of said wall where it is unclad into adjacent light curable dental material for substantially polymerizing said light curable dental material in a tray, said tray having a U-shaped bottom wall integrally connected to inner and outer U-shaped side walls.

33. The dental light of claim 32 wherein each of said unclad optic fibers is exposed for direct contact with the polymerizing light curable dental material in the mouth.

34. A method of polymerizing a light polymerizable elastomeric dental impression material in the shape of a U-shaped dental arch while said dental impression material is in contact with structure in the mouth, comprising: the steps of sequentially
   (a) providing a light source means for generating light having a U-shape adapted to distribute light from a curved side portion of a dental arch U-shape,
   (b) placing a dental impression material in a desired position in a mouth,
   (c) placing said light source in said mouth next to said dental impression material, and
   (d) emitting and transmitting light from said light source substantially uniformly directly over at least a substantial portion of an outwardly exposed surface of said dental impression material along a substantial portion of a dental arch U-shape to polymerize said material and form an elastomeric dental impression.

35. A dental light for polymerizing a light polymerizable elastomeric dental impression material while said dental impression material is in contact with structure in the mouth, comprising:
   (a) a light source being adapted to distribute light from and to be supported by a U-shaped dental arch and curved to conform with such substantial portion of said dental arch and sized to fit in a mouth in alignment with at least a portion of said dental arch, said light source transmitting light in said general configuration of said dental arch and said light source comprising light emitting and light transmitting sources selected from the group consisting of a series of light emitting devices and a plurality of light transmitting optic fibers and said light emitting and transmitting sources being positioned to emit and transmit light substantially uniformly over at least a substantial portion of an outwardly exposed surface of dental impression material in a tray placed in position for taking a dental impression in the mouth and sufficient to polymerize the dental impression material and form an elastomeric dental impression and a tray said tray having a U-shaped bottom wall integrally connected to inner and outer U-shaped side walls.

36. The method of claim 35 wherein said light source comprises a series of light emitting devices.

37. The method of claim 35 wherein said light source comprises a plurality of light transmitting optic fibers.

38. A visible wavelength light source apparatus for polymerizing light curable dental material in the mouth, comprising:
an element having a shape and size conforming to at least a curved substantial portion of a dental arch and adapted to support light curable dental material, and
optical fibers supported within said element and positioned along at least a majority of the length of said element, said element comprising a U-shaped tray and a housing, said housing having U-shaped bottom and inner and outer side walls connected to form a trough adapted to support light curable material, said tray being adapted to be positioned within said trough.

39. A visible wavelength light source apparatus for polymerizing light curable dental material in the mouth, comprising:
an element having a shape and size conforming to at least a curved substantial portion of a dental arch, and
means for generating light in said element, said means for generating light being positioned along at least a majority of the length of said element said element including two sides connected in a U-shape.

40. The apparatus of claim 39 further comprising a light transmitting means adapted to be removably connected to said element, said light transmitting means being adapted to hold said dental material in proximity to said element.

41. The apparatus of claim 39 wherein said means for generating light comprises a plurality of light sources.

42. A dental light for polymerizing light curable dental material in the mouth, comprising: a light source transmitting visible wavelength light and having a U-shape and size conforming substantially to a dental arch and sized to fit in the mouth, said light source comprising a plurality of at least partially unclad optic fibers formed into a web, each of said unclad optic fibers having a U-shaped length of unclad fiber wall and being adapted for transmitting light along at least a portion of said length and delivering said light from said unclad fiber wall for polymerizing said light curable dental material in the mouth.

43. A method of curing dental material, comprising:
providing an element having a U-shape and size conforming to a curved substantial portion of a dental arch and adapted to support light curable dental material, and optical fibers in said element positioned in a U-shape along at least a substantial portion of the length of said element,
positioning said element in a mouth adjacent to light curable dental material, and
transmitting light from said optical fibers in a U-shape to said curable dental material.

44. A method of curing dental material, comprising:
providing an element having a shape and size conforming to a curved substantial portion of a dental arch, and a light generator in said element positioned along at least a substantial portion of the length of said element,
positioning said element in a mouth adjacent to light curable dental material, and
transmitting light from said generator to said curable dental material wherein said light generator comprises a vacuum bulb.

45. A method of simultaneously uniformly curing dental impression material positioned in a patient's mouth, comprising simultaneously emitting light from a plurality of light emitting means positioned substantially uniformly along the length of said impression material.

46. The method of claim 45 wherein said light emitted from each of said light emitting means is of substantially equal intensity.

47. The method of claim 45 wherein said impression material and said light emitting means are supported in a U-shape.

48. A system for polymerizing light curable dental material in the mouth, comprising:
an element,
said element having a U-shape and size conforming substantially to a configuration of a dental arch,
means for generating light, said means for generating light comprising at least one electrical wire adapted to be connected to a power source, said means for generating light being supported by said element,
light transmitting means having a bottom member and two side members connected to said bottom member, and adapted to be positioned adjacent to said element, whereby light emitted from said element is transmitted through said light transmitting means into light curable dental material supported by said light transmitting means while said light transmitting means is in the mouth.

* * * * *

UNITED STATES PATENT AND TRADEMARK OFFICE
CERTIFICATE OF CORRECTION

PATENT NO. : 5,316,473
DATED : May 31, 1994
INVENTOR(S) : Robert V. Hare

It is certified that error appears in the above-indentified patent and that said Letters Patent is hereby corrected as shown below:

In claim 36, column 15, line 15 of the Patent change "method" to --dental light--.

In claim 37, column 15, line 17 of the Patent change "method" to --dental light--.

Signed and Sealed this

Thirtieth Day of May, 1995

Attest:

BRUCE LEHMAN

*Attesting Officer*     *Commissioner of Patents and Trademarks*